United States Patent [19]

Szantay et al.

[11] 4,329,350
[45] May 11, 1982

[54] 1,1-DISUBSTITUTED OCTAHYDRO-INDOLO[2,3-a]QUINOLIZINES, PROCESS FOR THE PREPARATION THEREOF AND COMPOSITIONS CONTAINING SAME

[75] Inventors: Csaba Szantay; Lajos Szabo; György Kalaus; Egon Karpati; Laszlo Szporny, all of Budapest, Hungary

[73] Assignee: Richter Gedeon Vegyeszeti Gyar R.T., Budapest, Hungary

[21] Appl. No.: 41,192

[22] Filed: May 21, 1979

Related U.S. Application Data

[63] Continuation-in-part of Ser. No. 10,720, Feb. 8, 1979, abandoned.

[30] Foreign Application Priority Data

Feb. 10, 1978 [HU] Hungary .................. RI 658

[51] Int. Cl.³ .................. A61K 31/40; C07D 455/02
[52] U.S. Cl. .................. 424/258; 546/70
[58] Field of Search .................. 546/70; 424/258

[56] References Cited

U.S. PATENT DOCUMENTS 4,052,404 10/1977 Szantay et al. .................. 546/70

Primary Examiner—Anton H. Sutto
Assistant Examiner—D. B. Springer

Attorney, Agent, or Firm—Karl F. Ross

[57] ABSTRACT

Compounds of the formula:

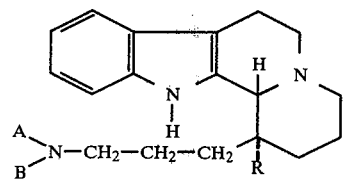

wherein
R is alkyl having 1 to 6 carbon atoms;
A is substituted or unsubstituted alkyl having 1 to 6 carbon atoms, aralkyl having 7 to 16 carbon atoms wherein the alkyl or aralkyl groups are unbranched in the 1-position or an acyl group derived from an aliphatic or aromatic carboxylic acid;
B is hydrogen; or
A and B together form an optionally substituted alkylidene having 2 to 8 carbon atoms or an aralkylidene group having 7 to 18 carbon atoms where the alkylidene and aralkylidene groups are unbranched in the 1-position or pharmaceutically acceptable salts thereof are disclosed. The compounds have vasodilating properties.

8 Claims, No Drawings

1,1-DISUBSTITUTED OCTAHYDRO-INDOLO[2,3-A]QUINOLIZINES, PROCESS FOR THE PREPARATION THEREOF AND COMPOSITIONS CONTAINING SAME

CROSS-REFERENCE TO RELATED APPLICATIONS

This application is a continuation-in-part of copending U.S. application Ser. No. 010,720 filed Feb. 8, 1979, now abandoned, and claiming a Hungarian priority date of Feb. 10, 1978.

The invention relates to new, racemic or optically active 1,1-disubstituted octahydro-indolo[2,3-a]quinolizines, pharmaceutically-acceptable salts thereof and to pharmaceutical compositions containing these compounds having valuable vasodilating properties.

More particularly, this invention concerns new, racemic or optically active compounds of the formula I

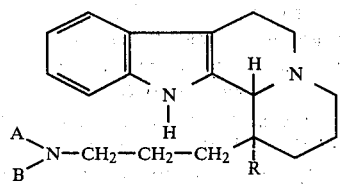

wherein
R is alkyl having 1 to 6 carbon atoms;
A is substituted or unsubstituted alkyl having 1 to 6 carbon atoms, aralkyl having 7 to 16 carbon atoms wherein the alkyl or aralkyl groups are unbranched in the 1-position or acyl derived from an aliphatic or aromatic carboxylic acid;
B is hydrogen; or
A and B together form an optionally substituted alkylidene having 2 to 8 carbon atoms or an aralkylidene having 7 to 19 carbon atoms—wherein the alkylidene and aralkylidene are unbranched in the 1-position,
and pharmaceutically-acceptable acid-addition salts thereof.

Closely related analogous compounds are described in U.S. Pat. No. 3,536,725. The disclosed 1-desalkyl-1-cyanoethyl-hexahydro-indolo[2,3-a]quinolizines are structurally different from the instant compounds in many respects. First of all, they contain a cyanoethyl group in the 1-position, while in the present invention 1-alkylamino, -aralyklamino, -alkylideneamino, -aralkylideneamino, and -acylamino compounds are described. Moreover, the instant compounds, without exception, contain an additional alkyl substituent in the 1-position, in contrast with the known compounds disclosed in the above patent specification, which are 1-desalkyl-derivatives. A further difference is that our compounds are octahydro-derivatives, while in the above reference hexahydro-derivatives are reported. Finally, most probably due to the structural difference, the compounds described in the U.S. Pat. No. 3,536,725 show no equivalent pharmaceutical activity, while the compounds according to the invention—as mentioned above—possess remarkable vasodilating properties.

The term "alkyl" as used in the definition of R and A means straight or branched chained saturated aliphatic hydrocarbon groups having 1 to 6, preferably 1 to 4, carbon atoms, e.g. methyl, ethyl, n-propyl, n-butyl, isobutyl, tert.-butyl, amyl, isoamyl, and hexyl. The alkyl group must be unbranched in the 1-position.

The term "aralkyl" in the definition of A is used to refer to hydrocarbon groups having 7 to 16 carbon atoms, in which the aryl moiety contains one or more aromatic rings, preferably one aromatic ring, and the alkyl moiety is a straight or branched chain saturated aliphatic hydrocarbon group having 1 to 6, preferably 1 to 4, carbon atoms that is unbranched in the 1-position. Typical representatives of said aralkyl groups are: benzyl, phenyl-ethyl, phenyl-propyl, phenyl-butyl, phenyl-amyl, phenyl-hexyl, as well as naphthyl-methyl, naphthyl-ethyl, naphthyl-propyl, naphthyl-butyl, naphthyl-amyl, and naphthyl-hexyl.

In the definition of A "acyl" is used to identify acyl groups derived from aliphatic or aromatic carboxylic acids.

As acyl groups derived from aliphatic carboxylic acids, acyl groups corresponding to saturated monobasic carboxylic acids, such as formic acid, acetic acid, propionic acid, butyric acid, and valeric acid should be mentioned. In the hydrocarbon moiety, which preferably has 1 to 6 carbon atoms, these acyl groups optionally contain one or more substituents, for example selected from the following group: halogen, e.g. fluorine, chlorine, bromine, iodine (which can be attached to the same or different carbon atoms, for example groups derived from monochloro-acetic acid, $\alpha,\beta$-dibromo-propionic acid, trifluoroacetic acid, $\gamma$-chloro-butyric acid), oxo group, amino group, and aryl group, such as phenyl, diphenyl, naphthyl group.

Acyl groups derived from aromatic carboxylic acids, which contain 6 to 14 carbon atoms in the hydrocarbon moiety may, for example, be selected from acyl groups derived from benzoic acid, diphenyl-carboxylic acids or naphthoic acids. In the aromatic nucleus these acyl groups optionally contain one or more substituents, for example $C_{1-6}$-alkyl, alkenyl or alkoxy, nitro, amino, hydroxy, trifluoromethyl, cyano, sulpho, thio, oxo, halogen substituents.

The alkylidene group obtained when A and B are attached together is a straight or branched chained alkylidene having 2 to 8, preferably 2 to 6, carbon atoms, such as ethylidene, propylidene, butylidene, pentylidene, hexylidene, heptylidene, and octylidene. The alkylidene group must be unbranched in the 1-position.

When A and B together are an aralkylidene group, this may stand for a group having 7 to 18, preferably 7 to 14, carbon atoms, for example benzylidene, phenyl-ethylidene, phenyl-propylidene, phenyl-butylidene, phenyl-pentylidene, and phenyl-hexylidene. Again the alkylidene group must be unbranched in the 1-position.

Where A and B are attached as indicated above to form an alkylidene or aralkylidene group the alkylidene group may be substituted by one or more substituents, for example selected from the following group: halogen, e.g. fluorine, chlorine, bromine and iodine (which can be attached to the same or different carbon atoms), an oxo group, amino group or aryl group such as phenyl, diphenyl, or naphthyl.

Where A and B are attached as indicated above to form an aralkylidene group the aryl group may contain one or more substituents, for example $C_1$ to $C_6$ alkyl, alkenyl or alkoxy or nitro, amino, hydroxy, trifluoromethyl, cyano, sulfo, thio, oxo or halo.

According to the invention the racemic or optically active compounds of the formula I—wherein R, A and B have the same meaning as defined above—and pharmaceutically-acceptable acid-addition salts thereof are prepared by reacting a 1-(3-aminopropyl)-octahydro-indolo[2,3-a]quinolizine of the formula

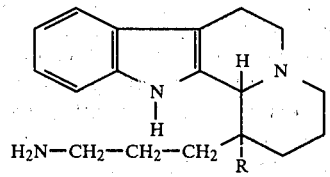

wherein R is as defined above—with a compound of the formula $$R'—CO—X \qquad (III)$$

or $$(R'—CO)_2O \qquad (IV)$$

wherein
R' is substituted or unsubstituted alkyl, aryl or aralkyl, in which the number of the carbon atoms corresponds to that of the desired end product after cleaving off a CO-group,
X is hydrogen, halogen or a hydroxyl group
and, if desired, reducing an acylamino or aldimino derivative obtained and/or, if desired, converting a 1,1-disubstituted-octahydro-indolo[2,3-a]quinolizine of the formula I obtained—wherein R, A and B are as defined above—into a pharmaceutically-acceptable acid-addition salt thereof and/or subjecting the same to resolution.

Starting compounds of the formula II are prepared according to British patent specification No. 1,518,696.

In the formulae III and IV, in the definition of R' "alkyl," "aryl" and "aralkyl" refer to groups listed in connection with R and A. In the definition of X the halogen may be selected from fluorine, chlorine, bromine and iodine.

If in the formula III X stands for a hydrogen atom, the reaction is performed with an approximately equimolar amount of the reactants having the general formulae II and III, respectively. The latter reactant may be used also in a slight excess, i.e. in a 1.1 to 1.8-fold molar quantity related to the starting compound of the formula II. The reaction is accomplished in a reaction-inert solvent, which can be a protic solvent, such as alcohols, e.g. methanol, ethanol; or an aprotic solvent, such as benzene, toluene etc.

In the latter case the water formed during the reaction is eliminated from the reaction mixture continuously, by azeotropic distillation.

Irrespective of the type of solvent used, the reaction is preferably carried out around the boiling temperature of the reaction mixture.

If in a compound of the formula III X represents a halogen atom, or if a compound of the formula IV is used as a second reactant, the reaction is preferably accomplished in the presence of an acid binding agent, to accelerate or complete the reaction. As an acid binding agent, organic bases, such as tertiary amines, e.g. triethyl amine, pyridine; or inorganic bases, such as alkali metal carbonates, e.g. sodium carbonate or potassium carbonate, or alkaline-earth metal oxides, e.g. magnesium oxide can be used. The reaction is performed in a reaction-inert organic solvent; but the excess of the reactant, for example a compound of the formula IV or the acid binding agent can also be used as a solvent.

If in the reactant of the formula III X represents a hydroxyl group, the reaction is preferably accelerated and completed by using a condensing agent, e.g. dicyclohexyl-carbodiimide.

If acylamino derivatives are obtained by the process according to the invention, they can be reduced to the corresponding alkylamino or aralkylamino derivatives. As a reducing agent, preferably a complex metal hydride, such as lithium aluminum hydride or borohydrides, preferably sodium borohydride, can be used in the presence of a metal salt, such as cobalt chloride. The reaction is accomplished in a reaction-inert organic solvent, such as ethers, for example, diethyl ether, tetrahydrofuran, etc., or alcohols, such as methanol, ethanol etc.

If aldimino derivatives are obtained by the process according to the invention, the corresponding alkylamino derivatives can be obtained also by reduction. The reduction can be performed either with a chemical reducing agent, for example with a complex metal hydride as described above, or with catalytically activated hydrogen. If the reduction is carried out with hydrogen, as a catalyst, a metal conventional for this purpose, such as palladium, platinum, nickel, iron, copper, cobalt, zinc, molybdenum, tungsten and the oxides and sulphides thereof can be used.

Catalytic hydrogenation can be accomplished also in the presence of catalysts precipitated on the surface of a carrier. Suitable carriers are for example coal, preferably charcoal, silica, alumina, and sulphates and carbonates of alkali earth metals.

In the process according to the invention, preferably palladium, more preferably palladium-on-charcoal or Raney nickel are used as catalysts, but the selection of the catalyst always depends on the properties of the compound subjected to hydrogenation and on the reaction conditions.

Catalytic hydrogenation is carried out in a reaction-inert solvent, for example, in an alcohol, ethyl acetate, glacial acetic acid or in optional mixtures of the above solvents. The most preferred solvents are alcohols, such as methanol, ethanol. If platinum oxide is used as a catalyst, it is preferred to work in a neutral, or rather acid medium; while when using a Raney nickel catalyst, the reaction medium preferably is neutral or alkaline.

The temperature, pressure and reaction time of the catalytic hydrogenation according to the invention can be varied within a wide range, depending on the starting compound; it is preferred, however, to perform the reaction at room temperature, under atmospheric pressure.

Compounds of formula I—wherein R, A and B are as defined above—prepared according to the invention, if desired, can be converted into pharmaceutically-acceptable acid-addition salts. Suitable acids for this reaction are inorganic acids, such as hydrogen halides, such as hydrochloric acid, hydrogen bromide, phosphorous acid; organic carboxylic acid, hydrogen bromide, phosphorous acid; organic carboxylic acids, such as acetic acid, propionic acid, glycolic acid, maleic acid, succinic acid, tartaric acid, citric acid, salicylic acid, benzoic acid; alkyl-sulphonic acids, such as methanesulfonic acid, or aryl-sulphonic acids such as p-toluene-sulphonic acid.

Salts are preferably prepared in an inert solvent, more preferably in an aliphatic alcohol, such as methanol. The base of formula I is dissolved in said solvent and the aqueous or alcoholic solution of the corresponding acid is added until a slightly acidic (having a pH of about 6) mixture is obtained. The salt precipitated from the reaction mixture is thereafter isolated, preferably by precipitation with a water-immiscible organic solvent, such as diethyl ether.

Compounds of formula I prepared as described hereinbefore—wherein R, A and B are as defined above—if desired, can be subjected to further purification steps, for example, recrystallization.

Compounds of formula I—wherein R, A and B are as defined above—contain an asymmetric carbon atom, and consequently have two optically active antipodes. The process relating to the separation of the individual optical antipodes is also within the scope of the invention. The resolution can be accomplished with techniques conventional for this purpose.

The process according to the invention provides compounds of formula I with an excellent yield, in a form easy to identify. The results of the elementary analysis show a good agreement with the calculated values, and the characteristic IR peaks also prove unambiguously that the compounds have a structure represented by formula I.

The most preferred compounds within the scope of this invention are as follows:

1α-ethyl-1-(3-acetaminopropyl)-1,2,3,4,6,7,12,12bβ-octahydro-indolo[2,3-a]quinolizine and dihydrogen chloride thereof;

1α-ethyl-1-(3-ethylaminopropyl)-1,2,3,4,6,7,12,12bβ-octahydro-indolo[2,3-a]quinolizine and dihydrogen chloride thereof;

1α-ethyl-1-(3-butylideneaminopropyl)-1,2,3,4,6,7,12,12bβ-octahydro-indolo[2,3-a]quinolizine;

1α-ethyl-1-(3-butyrylaminopropyl)-1,2,3,4,6,7,12,12bβ-octahydro-indolo[2,3-a]quinolizine;

1α-ethyl-1-(3-butylaminopropyl)-1,2,3,4,6,7,12,12bβ-octahydro-indolo[2,3-a]quinolizine;

1α-ethyl-1-(3-benzoylaminopropyl)-1,2,3,4,6,7,12,12bβ-octahydro-indolo[2,3-a]quinolizine;

1α-ethyl-1-(3-benzylaminopropyl)-1,2,3,4,6,7,12,12bβ-octahydro-indolo]2,3-a]quinolizine;

1α-ethyl-1-[3-(3',4',5'-trimethoxybenzoylamino)-propyl]-1,2,3,4,6,7,12,12bβ-octahydro-indolo[2,3-a]quinolizine;

1α-ethyl-1-[3-(3',4',5'-trimethoxybenzylamino)-propyl]-1,2,3,4,6,7,12,12bβ-octahydro-indolo[2,3-a]quinolizine.

Tests carried out on narcotized dogs show that the compounds of formula I possess a remarkable vasodilating activity, and especially are capable of increasing the extremital and cerebral blood stream to a considerable extent.

For these tests dogs narcotized with "chloralose-urethane" were used. Extremital blood stream was measured on the femoral artery, cerebral blood stream was determined on the basis of measurements on internal carotis, while circular vein resistances were calculated from corresponding values of blood pressure and blood stream.

The test compounds were administered intravenously, in a dose of 1 mg./kg. The percentage changes were calculated. The average of the results obtained on six animals are indicated in the following Table I.

For comparison, in the same Table I the corresponding values obtained with apovincaminic acid ethyl ester are also given. This compound has been selected for comparison, since until now it proved to be the most active out of the chemically related compounds.

In the different columns of Table I the following parameters are indicated:
1. Extremital blood stream
2. Extremital circulation resistance
3. Cerebral blood stream
4. Cerebral circulation resistance
5. Blood pressure
6. Heart frequency

TABLE I

The average of percentage changes induced with a 1 mg./kg. i.v. dose of the test compounds:

| Compound | 1. | 2. | 3. | 4. | 5. | 6. |
|---|---|---|---|---|---|---|
| apovincaminic acid ethyl ester | +58 | −35 | +16 | −20 | −28 | +14 |
| compound of Example 1 | +101.6 | −70.8 | +47.3 | −57.1 | −12.9 | +34 |
| compound of Example 2 | +148 | −72.4 | +5.6 | −22.2 | −19.4 | −8.4 |

From the data indicated in the above Table it can be seen that the circulation stimulating activity of the test compound is 2 to 2.5-fold of that of the reference compound. Regarding the cerebral vasodilating activity, the test compounds are three times as active as the reference compound.

The effective dose of the instant compounds, when administered intravenously or orally should range from several tens of milligrams to 1 to 2 mg. per kg. of body weight. The actual dose should, however, be selected according to the state of the patient and the experiences of the doctor, in line with the requirements of the given case. It should, therefore, be emphasized that the above-indicated doses do not limit the scope of this invention in any respect.

The new compounds of formula I or the pharmaceutically-acceptable acid-addition salts or optically-active isomers thereof may be formulated for therapeutic purposes. The invention therefore also relates to pharmaceutical formulations containing at least one compound of formula I—wherein R, A and B are as described above—or pharmaceutically-acceptable salts thereof, in admixture with inert, non-toxic carriers conventional for this purpose and suitable for parenteral or enteral administration and/or other additives. As carriers solid or liquid compounds, for example water, gelatine, lactose, milk sugar, starch, pectine, magnesium stearate, stearic acid, talc, vegetable oils, such as peanut oil, olive oil, gummi arrabicum, polyalkylene glycols, vaseline can be used. The compounds can be formulated as conventional pharmaceutical formulations, for example in a solid (globular and angular pills, suppositories) or liquid (oily or aqueous solutions, suspensions, emulsions, syrups, soft gelatine capsules, injectable oily or aqueous solutions or suspensions) form. The quantity of the solid is between 25 mg. and 1 g. The compositions optionally contain also conventional pharmaceutical additives, such as preserving agents, stabilizing agents, emulsifying agents, wetting agents, salts for adjusting the osmotic pressure, buffers, flavoring and aromatic materials. The compositions according to the invention optionally contain the compounds of formula I in association with other, known active ingredients. The unit doses are selected depending on the method of administration. The pharmaceutical compositions are prepared by conventional techniques including sieving, mixing, granulation, pressing or dissolution of the ingredients. The formulations obtained are then subjected to additional conventional treatments, such as sterilization.

Further details of the invention are illustrated by the following non-limiting Examples.

EXAMPLE 1

1α-ethyl-1-(3-acetaminopropyl)-1,2,3,4,6,7,12,12bβ-octahydro-indolo[2,3-a]quinolizine 4.2 g (13.5 mmoles) of 1α-ethyl-1-(3-aminopropyl)-1,2,3,4,6,12,12bβ-octahydro-indolo[2,3-a]quinolizine are dissolved in 70 ml of absolute pyridine, 15 ml of acetic anhydride are added to the solution obtained, and the reaction mixture is allowed to stand at room temperature overnight. The solvent and the excess of the reactant are eliminated in vacuo, the oily residue is triturated with a 5% aqueous sodium bicarbonate solution and allowed to stand. After several hours the solidified oil is filtered off, washed with water, and the substance obtained is recrystallized from a mixture of methanol and water.

2.5 g of the named compound are obtained, as a crystalline product.

Melting point: 126° C. to 128° C.

Analysis for $C_{22}H_{31}N_3O$ (molecular weight: 353.49): Calculated: C=74.74%; H=8.84%; N=11.88%; Found: C=74.59%; H=8.63%; N=11.52%.

IR-spectrum (KBr): $\nu_{max}$=3230 cm$^{-1}$ (indole-NH); 2870 to 2730 cm$^{-1}$ (Bohlman bands); 1660 to 1620 cm$^{-1}$ (=C=O).

EXAMPLE 2

1α-Ethyl-1-(3-ethylaminopropyl)-1,2,3,4,6,7,12,12bβ-octahydro-indolo[2,3-a]quinolizine dihydrogen chloride 1.8 g (5.1 mmoles) of 1α-ethyl-1-(3-acetaminopropyl)-1,2,3,4,6,7,12,12bβ-octahydro-indolo[2,3-a]quinolizine prepared in Example 1 are suspended in 200 ml. of absolute ether and 1.5 g. (39.6 mmoles) of lithium aluminum hydride are added to the suspension. The reaction mixture is stirred at room temperature for 30 minutes, then refluxed for 4 additional hours. The solution obtained is cooled, 100 ml. of a saturated solution of Seignette-salt (potassium sodium tartarate) is added and after some minutes of stirring the aqueous layer is separated. The aqueous solution is shaken with 50 ml. of ether, whereupon the combined etheralsolution is dried over anhydrous magnesium sulphate, filtered and from the filtrate the solvent is eliminated. The remaining solidifying oil is dissolved in a small amount of ethanol, then the pH of the solution is adjusted to slightly acidic by adding methanol saturated with hydrochloric acid gas. The slightly acidic solution is diluted with ether, whereupon the precipitated substance is filtered, washed and dried.

1.65 g. of the named compound are obtained in the form of white crystals.

Yield: 78.9%

Melting point: 227° to 229° C. (foaming)

Analysis for $C_{22}H_{33}N_2$. 2HCl (molecular weight: 4.2.43): Calculated: C=64.06%; H=8.55%; N=10.18%; Found: C=63.87%; H=8.39%; N=9.91%.

IR spectrum (KBr): $\nu_{max}$=3300 cm (indole-NH); 2900 to 2700 cm$^{-1}$ (Bohlmann bands).

EXAMPLE 3

1α-Ethyl-1-(3-acetaminopropyl)-1,2,3,4,6,7,12,12bβ-octahydro-indolo[2,3-a]quinolizine-containing tablet

| | |
|---|---|
| 1α-ethyl-1-(3-acetaminopropyl)-1,2,3,4,6,7,12,12bβ-octahydroindolo[2,3-a]quinolizine (active ingredient) | 5 mg |
| gelatine | 3 mg |
| magnesium stearate | 2 mg |
| talc | 5 mg |
| potato starch | 40 mg |
| milk sugar | 95 mg |

The active ingredient is admixed with ¾ amount of the potato starch and with the milk sugar. The homogenous mixture obtained is kneaded with an aqueous solution of gelatine, granulated and dried. Talc and the remaining part of potato starch together with magnesium stearate are added into the dried granules obtained, and the mixture is pressed into tablets. If desired, the tablets are equipped with grooves to make administration easier.

EXAMPLE 4

1α-ethyl-1-(3-benzylaminopropyl)-1,2,3,4,6,7,12,12bβ-octahydro-indolo[2,3-a]quinolizine 1.00 g (3.21 mmoles) of 1α-ethyl-1-(3-aminopropyl)-1,2,3,4,6,7,12,12bβ-octahydro-indolo[2,3-a]quinolizine is dissolved in 20 ml. of absolute methanol. 0.50 g (0.48 ml. 4.71 mmoles) benzoic aldehyde are added to the solution, and the reaction mixture is refluxed for 48 hours. After the refluxing 30 ml. of methanol again were added to the solution and the reaction mixture is cooled to 0° C. At the same temperature 1.50 g (3.96 mmoles) of sodium borohydride are added in small portions to the mixture with constant stirring. Thereafter the mixture is stirred at 0° C. for 1 hour. After stirring, the solution is acidified with 5 N aqueous hydrochloric acid to pH 2, whereupon the mixture is evaporated in vacuo to a volume of 10 ml. The residue is dissolved in 100 ml. of water and the solution is made basic by adding 40% aqueous sodium hydroxide solution to pH 10. The basic solution is shaken with 50, 30 and 20 ml. dichloromethane. The combined organic solution is dried over magnesium sulphate, filtered and evaporated in vacuo. The remaining oil is crystallized from methanol.

0.80 g of the named compound are obtained in the form of white crystals.

Yield: 62%

Melting point: 109° to 110° C.

Calculated: C 80.75%; H 8.78%; N 10.18%; Found C 80.65%; H 8.74%; N 10.64%.

| NMR Spectra (CDCl$_3$) | |
|---|---|
| Delta: 0.63 | /T, 3H, CH3-/, |
| Delta: 3.42 | /S, 1H, Annellated H/, |
| Delta: 3.92 | /S, 2H, Benzyl-CH2-/, |
| Delta: 6.83-7.62 | /M, 9H, Aromatic H/, |
| Delta: 10.60 | /S, 1H, Indole-NH/. |

We claim:
1. A compound of the formula:

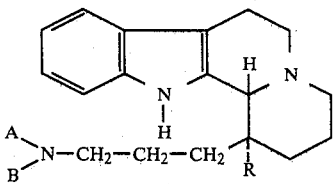

wherein

R is alkyl having 1 to 6 carbon atoms;

A is $C_1$ to $C_6$ alkyl where the alkyl is unbranched in the 1-position; phenyl- or naphthyl-$C_1$ to $C_6$ alkyl where the alkyl is unbranched in the 1-position; methoxy-phenyl- or methoxy-naphthyl-$C_1$ to $C_6$ alkyl where the alkyl is unbranched in the 1-position; $C_1$ to $C_7$ alkanoyl; benzoyl or methoxybenzoyl; and B is hydrogen;

or a pharmaceutically acceptable acid addition salt thereof.

2. The compound defined in claim 1 which is 1α-ethyl-1-(3-acetaminopropyl)-1,2,3,4,6,7,12,12bβ-octahydro-indolo[2,3-a]quinolizine.

3. The compound defined in claim 1 which is 1α-ethyl-1-(3-ethylaminopropyl)-1,2,3,4,6,7,12,12bβ-octahydro-indolo[2,3-a]quinolizine, or the dihydrogen chloride thereof.

4. The compound defined in claim 1 which is 1α-ethyl-1-(3-butyrylaminopropyl)-1,2,3,4,6,7,12,12bβ-octahydro-indolo[2,3-a]quinolizine.

5. The compound defined in claim 1 which is 1α-ethyl-1-(3-benzoylaminopropyl)-1,2,3,4,6,7,12,12bβ-octahydro-indolo[2,3-a]quinolizine.

6. The compound defined in claim 1 which is 1α-ethyl-1-(3-benzylaminopropyl)-1,2,3,4,6,7,12,12bβ-octahydro-indolo[2,3-a]quinolizine.

7. A pharmaceutical composition having vasodilating activity, which comprises an effective amount of a 1,1-disubstituted octahydro-indolo[2,3-a]quinolizine of the formula:

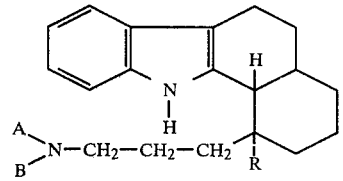

wherein

R is alkyl having 1 to 6 carbon atoms;

A is $C_1$ to $C_6$ alkyl where the alkyl is unbranched in the 1-position; phenyl- or naphthyl-$C_1$ to $C_6$ alkyl where the alkyl is unbranched in the 1-position; methoxy-naphthyl-$C_1$ to $C_6$ alkyl where the alkyl is unbranched in the 1-position; $C_1$ to $C_7$ alkanoyl; benzoyl or methoxybenzoyl; and B is hydrogen;

or a pharmaceutically acceptable acid addition salt thereof, as active ingredient, in admixture with a pharmaceutical excipient.

8. A method of treating an animal subject to induce vasodilating which comprises administering to said subject an effective amount of a compound as defined in claim 1 or a pharmaceutically acceptable salt thereof.

* * * * *